(12) United States Patent
Xiu

(10) Patent No.: US 6,887,500 B2
(45) Date of Patent: May 3, 2005

(54) COMPOSITIONS FOR LOWERING BLOOD PRESSURE

(76) Inventor: Rulin Xiu, 2702 13$^{th}$ St., NW., Washington, DC (US) 20009

( * ) Notice: Subject to any disclaimer, the term of this patent is extended or adjusted under 35 U.S.C. 154(b) by 135 days.

(21) Appl. No.: 10/429,877

(22) Filed: May 6, 2003

(65) Prior Publication Data

US 2004/0086584 A1 May 6, 2004

Related U.S. Application Data

(60) Provisional application No. 60/422,871, filed on Nov. 1, 2002.

(51) Int. Cl.$^7$ .......................... A61K 33/00; A61K 35/78
(52) U.S. Cl. ....................... 424/765; 424/771; 424/774; 424/776
(58) Field of Search ................................ 424/765, 771, 424/774, 776, 725

(56) References Cited

U.S. PATENT DOCUMENTS 4,059,695 A     11/1977  Hirosaki et al.
5,665,359 A  *  9/1997   Ho et al. ..................... 424/765
6,087,107 A  *  7/2000   Sheffield et al. ............... 435/6
6,416,807 B1 *  7/2002   Yamamoto ................... 426/597

FOREIGN PATENT DOCUMENTS

JP           411269082 A   * 10/1999

* cited by examiner

*Primary Examiner*—Brenda Brumback
*Assistant Examiner*—Randall Winston
(74) *Attorney, Agent, or Firm*—Millen, White, Zelano & Branigan, P.C.

(57) ABSTRACT

The present invention relates to natural compositions for lowering blood pressure, and treating various conditions associated with the occurrence of high blood pressure. These compositions can comprise two or more of the following ingredients in amounts which are effective to treat blood pressure conditions, e.g., (a) Hainan Holly leaf (e.g., *Ilex hainanensis* Merr.), (b) Chinese Hawthorn fruit (e.g., *Crataegus pinnatifida* Bge. or *Crataegus cuneata* Sieb. et Zucc.), (c) Garden radish seed (*Raphanus sativus* L.), and (d) Oriental persimmon leaf (*Diospyros kaki* L.f).

11 Claims, 2 Drawing Sheets

The Average Systolic Blood Pressures at the End of 0, 2$^{nd}$, 4$^{th}$, 6$^{th}$, 8$^{th}$, 12$^{th}$ Week of the Subjects Taking Holistrol (Product Group) or Placebo for 8 Weeks The Average Diastolic Blood Pressures at the End of 0, 2nd, 4th, 6th, 8th, 12th Week of the Subjects Taking Holistrol (Product Group) or Placebo for 8 Weeks

COMPOSITIONS FOR LOWERING BLOOD PRESSURE

This application claims the benefit of U.S. Ser. No. Provisional Application 60/422,871, filed Nov. 1, 2002, which is hereby incorporated by reference in its entirety.

BACKGROUND OF THE INVENTION

Hypertension, or high blood pressure, is the leading reason for office visits to physicians in United States, affecting more than a quarter of US population. It is a dangerous condition that can lead to stroke, enlarged heart, congestive heart failure, kidney and eye damage, arteriosclerosis, blindness, and premature death. Hypertension is the No. 1 modifiable risk factor for stroke. Compared to people with controlled high blood pressure, people with uncontrolled high blood pressure are three times more likely to develop coronary heart disease, six times more likely to develop congestive heart failure, and seven times more likely to have a stroke.

Hypertension is the No. 1 uncontrolled silent killer worldwide. In US, only 27 percent of persons with hypertension are currently achieving successful control of their condition, 32 percent of all people with hypertension are unaware of their condition and are not receiving treatment, 15 percent are aware of it but are not receiving treatment, and 26% have treated but uncontrolled hypertension.

Many factors lead to the epidemic of hypertension. First of all, the compliance with drug treatment of hypertension is difficult for many people. The current drug treatment of hypertension only controls the symptoms of hypertension. This means that people need to take the hypertension drugs for the rest of their life once they start drug treatment. In fact, it is even more dangerous for people to stop taking drug treatment once they start since the rapid changes of blood pressure will do more damage to the body. Secondly, the various side effects of hypertension drugs, including lethargy, impotence, depression, and increased triglyceride and cholesterol levels, often deter many people from taking the medicines. Another astonishing factor is that nearly one third of people having hypertension do not even know they have this life-threatening condition.

According to recent survey by Roper Starch Worldwide/ Consumer Healthcare Products Association, more than half of Americans would like to be more active in supporting their health before resorting to prescription medications.

DESCRIPTION OF THE INVENTION

Figure 1:
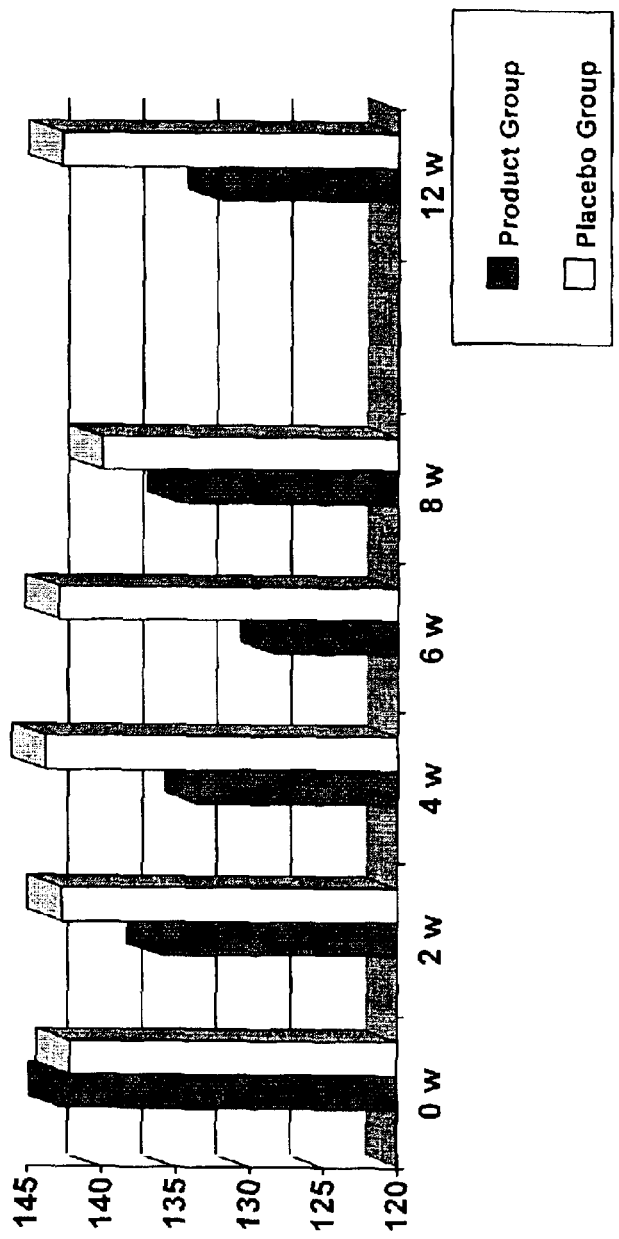
FIG. 1 shows the average systolic pressure of subjects taking Holistrol ("product group") and placebo.

The present invention relates to natural compositions for lowering blood pressure, and treating various conditions associated with the occurrence of high blood pressure. These compositions can comprise two or more of the following ingredients in amounts which are effective to treat blood pressure conditions, e.g., (a) Hainan Holly leaf (e.g., *Ilex hainanensis* Merr.), (b) Chinese Hawthorn fruit (e.g., *Crataegus pinnatifida* Bge. or *Crataegus cuneata* Sieb. et Zucc.), (c) Garden radish seed (e.g., *Raphanus sativus* L.), and (d) Oriental persimmon leaf (e.g., *Diospyros kaki* L.f).

In a double blind, placebo-controlled human clinical study, 16 patients with mild to moderate hypertension (<159/99) took a composition of the present invention for three times a day for two months. The average decrease of the systolic blood pressure was about 17.57 points (12%) and that of diastolic blood pressure was about 13.86 point (15%), while that of the placebo group was only about 0.75 and 5.50 points respectively. The blood pressures of many of the patients taking these compositions returned to a normal range within about two weeks. Strikingly, after stopping taking these compositions for a month, the blood pressure of about half of the study group members still remained within the normal range. Thus, unlike many prescription drugs, compositions of the present invention maintain blood pressure at normal levels even after therapy has ceased. In addition to experiencing beneficial effects on blood pressure levels, several subjects taking these compositions also reported improvements in energy and mood.

Accordingly, the present invention relates to methods of lowering blood pressure in a subject in need thereof, comprising, e.g., administering effective amounts of at least two herbs selected from the group consisting of Hainan holly leaf, Chinese hawthorn fruit, Garden radish seed, and Oriental persimmon, wherein said amounts are effective to lower blood pressure.

By the phrase "lowering blood pressure," it is meant that the blood pressure in a subject is reduced upon intake of a composition in accordance with the present invention. Any amount of blood pressure lowering is acceptable, as long as it is reduced by a statistically significant amount. Blood pressure is typically represented as systolic pressure over diastolic pressure. The systolic pressure refers to the pressure in the arterial system at its highest, and diastolic pressure refers to the lowest pressure. It is usually measured at the brachial artery with a sphygmomanometer (pressure cuff) in mm of Hg. Normal pressure is 120/70 on average, but normal for an individual can vary with the height, weight, fitness level, health, emotional state, age, etc., of a person. Although there is no clear dividing line between normal and high blood pressure, arbitrary levels have been established to define those have an increased risk of adverse developing cardiovascular events. For example, a diastolic pressure below 85 mmHg is considered to be normal, between 85–89 is high normal, 90–104 is mild hypertension, 105–114 moderate hypertension, and 115 or greater is considered severe hypertension. When the diastolic is below 90 mmHg, a systolic pressure below 140 mmHg is normal blood pressure, between 140–159 is borderline isolated systolic hypertension, and 160 and higher is isolated systolic hypertension.

Compositions of the pressure invention can be used to lower blood pressure, e.g., by 2%, 5%, 10%, 12%, 15%, 20%, etc., and can lower systolic and/or diastolic blood pressure. Chronically high blood pressure is called hypertension and is a life threatening condition that must be managed and or treated. The present invention can also be used to treat any type of hypertension, including, e.g., labile hypertension (e.g., patients who do not always have blood pressures in the hypertension range), sustained hypertension, malignant, accelerated, mild, borderline, severe, primary, essential, idiopathic, renal hypertension, endocrine hypertension, secondary hypertension, neurogenic etc. The term "treating" is used conventionally, e.g., the management or care of a subject for the purpose of combating, alleviating, reducing, relieving, improving the condition of, etc., of hypertension and any associated or secondary symptoms, conditions, or diseases.

The amounts of the ingredients, individually or in combination, are effective in lowering blood pressure. An "effective amount" indicates that the mass of ingredient or ingredients in the composition is useful to achieve the purpose for which it is administered. Amounts are selected based on various factors, including age, health, gender, weight, severity of condition, general health, age, etc, of a patient to be treated. Useful amounts include (in grams), e.g., about 0.5–20, 0.5–5, 0.5–3, 0.5–2, 0.5–1.5, 0.5, 1, 1.5, 2, 3, etc., a day. These can be administered in any individual dosage which is effective, e.g., (in grams), about 0.1, 0.2, 0.3, 0.4, 0.5, 0.75, 1, 1.25, 1.5, 2, 5, etc. The amounts can be administered 1, 2, 3, 4, 5, 6, etc. times a day, e.g., depending upon the subject's physical condition, the severity of the disease, etc.

The ingredients can be combined in "synergistic amounts." By this, it is meant that the amounts of the ingredient present in the composition (and in combination with the other ingredients) is more effective at achieving the desired purpose (e.g., reducing blood pressure) than when administered alone or in another herbal composition. Synergy indicates that the ingredients cooperate with each other to achieve an enhanced or superior result than would be achieved if either were administered alone, i.e., the effect is not additive (the sum is greater than the sum of the individual parts).

The present invention also relates to pharmaceutical compositions, comprising, e.g., effective amounts of at least two herbs selected from the group consisting of Hainan holly leaf, Chinese hawthorn fruit, Garden radish seed, and Oriental persimmon, wherein said composition is effective for lowering blood pressure.

To achieve blood pressure lowering, a composition in accordance with the present invention is administered to a subject. By the term "administered," it is meant that the composition is delivered to a subject by any means or route which is effective to achieve the desired result, including, e.g., oral, parenteral, enteral, intraperitoneal, topical, transdermal (e.g., using any standard patch), ophthalmic, nasally, local, non-oral, such as aerosol, inhalation, subcutaneous, intravenous, intramuscular, buccal, sublingual, rectal, vaginal, intra-arterial, intrathecal. Compositions can be administered at any time suitable time, e.g., prior or after a meal, prior to exercise, prior to activity, prior to sleeping, in the morning, etc.

The compositions can be in any effective form, including, oral, pill, capsule, troche, liquid, extract, beverage, food, tea, topical, injectable, etc. They can be administered alone, or in combination with other active or inert agent(s).

Any effective part of an herb in accordance with the present invention can be used, including to seeds, leaves, stems, flowers, roots, berries, bark, fruit or any other plant parts that are useful for the purposes described. Herbs can be in any form which is effective, including, but not limited to dry powders, grounds, emulsions, extracts, and other conventional compositions. To extract or concentrate the effective ingredients of an herb, typically the plant part is contacted with a suitable solvent, such as water, alcohol, methanol, or any other solvents, or mixed solvents. The choice of the solvent can be made routinely, e.g., based on the properties of the active ingredient that is to be extracted or concentrated by the solvent.

Herbs can be used as 5:1 extract, e.g., an aqueous extract. This indicates that the dry weight of the herb is concentrated five times (5:1) in the extract. Any of the aforementioned formula can be prepared with a 5:1 extract, and any of the aforementioned values can refer to the weight of the extract.

A composition can comprise one or more of the following ingredients by weight, preferably two or more, and most preferably all four ingredients. These ingredients can be administered in one unit dosage, but also can be administered in separate dosage units, e.g., four different pills, each pill containing one herb, two different pills, each pill containing two different herbs, etc.

(a) Hainan Holly leaf (e.g., *Ilex hainanensis* Merr.), e.g., from about 10–95% by weight of the composition, e.g., in a 5:1 powder extract;

(b) Chinese Hawthorn fruit (e.g., *Crataegus pinnatifida* Bge. or *Crataegus cuneata* Sieb. et Zucc.), e.g., from about 2–50% by weight of the composition, e.g., in a 5:1 powder extract;

(c) Garden radish seed (*Raphanus sativus* L.), e.g., from about 2–50% by weight of the composition, e.g., in a 5:1 powder extract; or (d) Oriental persimmon (*Diospyros kaki* L.f), e.g., 2–60% by weight of the composition, e.g., in a 5:1 powder extract.

Preferred compositions include (by weight of the composition), e.g., (a) Hainan Holly leaf, about 75–80%, (b) Chinese Hawthorn fruit, about 3–5%, (c) Garden radish, about 3–5%; and (d) Oriental persimmon, 8–10%;

(a) Hainan Holly leaf, about 88–91%, (b) Chinese Hawthorn fruit, about 3–4.5%, (c) Garden radish, about 3–4.5%;

(a) Hainan Holly leaf, about 35–40%, (b) Chinese Hawthorn fruit, about 5–10%, (c) Garden radish, about 5–10%; and (d) Oriental persimmon, 30–40%;

(a) Hainan Holly leaf, about 75–80%, and (b) Oriental persimmon, 15–20%;

(a) Hainan Holly leaf, about 75–80%, and (b) Garden radish, about 15–20%;

(a) Hainan Holly leaf, about 75–80%, (b) Chinese Hawthorn fruit, about 15–20%, (a) Hainan Holly leaf, about 35–40%, (b) Chinese Hawthorn fruit, about 3–5%, and (c) Oriental persimmon, 45–55%.

(a) 85–95% by weight of Hainan holly leaf, (b) 2–5% by weight of Chinese Hawthorn fruit, and (c) 2–5% by weight of Garden radish.

Compositions can further comprise inert and carrier ingredients, stabilizers, anti-oxidants, etc., including, but not limited to, water, salt solutions, alcohols, gum arabic, vegetable oils, benzyl alcohols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose and the like. Other additives include, e.g., antioxidants and preservatives, coloring, flavoring and diluting agents, emulsifying and suspending agents, such as acacia, agar, alginic acid, sodium alginate, bentonite, carbomer, carrageenan, carboxymethylcellulose, cellulose, cholesterol, gelatin, hydroxyethyl cellulose, hydroxppropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, and miscellaneous ingredients such as microcrystalline cellulose, citric acid, dextrin, dextrose, liquid glucose, lactic acid, lactose, magnesium chloride, potassium metaphosphate, starch, and the like.

Compositions of the present invention can also be formulated with other active ingredients, such as anti-oxidants, vitamins (A, C, ascorbic acid, B vitamins, such as B1, thiamine, B6, pyridoxine, B complex, biotin, choline, nicotinic acid, pantothenic acid, B12, cyanocobalamin, and/or B2, D, D2, D3, calciferol, E, such as tocopherol, riboflavin, K, K1, K2), creatine monohydrate, pyruvate, L-Carnitine, alpha-lipoic acid, Phytin or Phytic acid, Co Enzyme Q10, NADH, NAD, D-ribose, amino acids such as L-Glutamine, Lysine, chrysin, etc.

Other plants and herbs which can be formulated with a composition of the present invention includes those mentioned in various text and publications, e.g., *ES Ayensu, Medicinal Plants of West Africa*, Reference Publications, Algonac, MI (1978); P. Back, *The Illustrated Herbal* 1987, Hamlyn Publishers, distributed by Octopus Books, Printed in Hong Kong by Mandarin, ISBN 0-600 553 361; F. Bianchini and F. Corbetta, *The Fruits of the Earth*, translated from Italian by A. Mancinelli, Bloomsbury Books, London, ISBN 1-870630-10-6; H. M. Burkill, *The Useful plants of West Tropical Africa*, Ed. 2, V. 1, Royal Botanic Gardens Kew, ISBN 0-947643-01-X (1985); L. Boulos, *Medicinal Plants of North Africa*, Reference Publications Inc., Algonac, MI (1983); and N. C. Shah, *Herbal Folk Medicines in Northern India*, J. Ethnopharm, 6:294–295 (1982).

Compositions of the present invention can be combined with other treatments, including treatments involving behavioral therapy, diet restrictions, surgical intervention, and pharmacological intervention. There are many different drugs which are used to treat hypertension, and these can be combined with the compositions of the present invention As discussed earlier, hypertension can cause serious medical complications, including stroke, enlarged heart, congestive heart failure, kidney and eye damage, arteriosclerosis, and premature death. Compositions of the present invention, when used to treat high blood pressure in a subject, can also treat any of the secondary symptoms.

EXAMPLE

A randomized and placebo-controlled study was conducted over a 3-month period. There were ten patients in the placebo group, and nine in the group taking a composition of the present invention ("Holistrol"). The placebo and composition of the present invention were randomized and masked, so participants nor study personnel knew whether they were receiving the active composition. Subjects were recruited from the general population. Subjects had not received any blood pressure medication for at least one-month prior to the study. Informed consent was received, and IRB approval was obtained at all stages of the study.

Each participant took 6 capsules daily, 2 in the morning, 2 at noon, and 2 in the evening with food. Each capsule contained 275 mg. A unit dosage (1 capsule) contained the following amounts of active ingredients: Hainan Holly leaf, about 91% by weight, Chinese Hawthorn fruit, about 4.5% by weight, and Garden radish, about 4.5% by weight. The treatment was stopped after two-months, and patients were followed up for the third-month.

Results: FIG. 1 shows the average systolic pressure of subjects taking Holistrol ("product group") and placebo. The data is also summarized in Table 1. The results show that the decrease in blood pressure was sustained even after the Holistrol had been stopped for a month.

Figure 2:
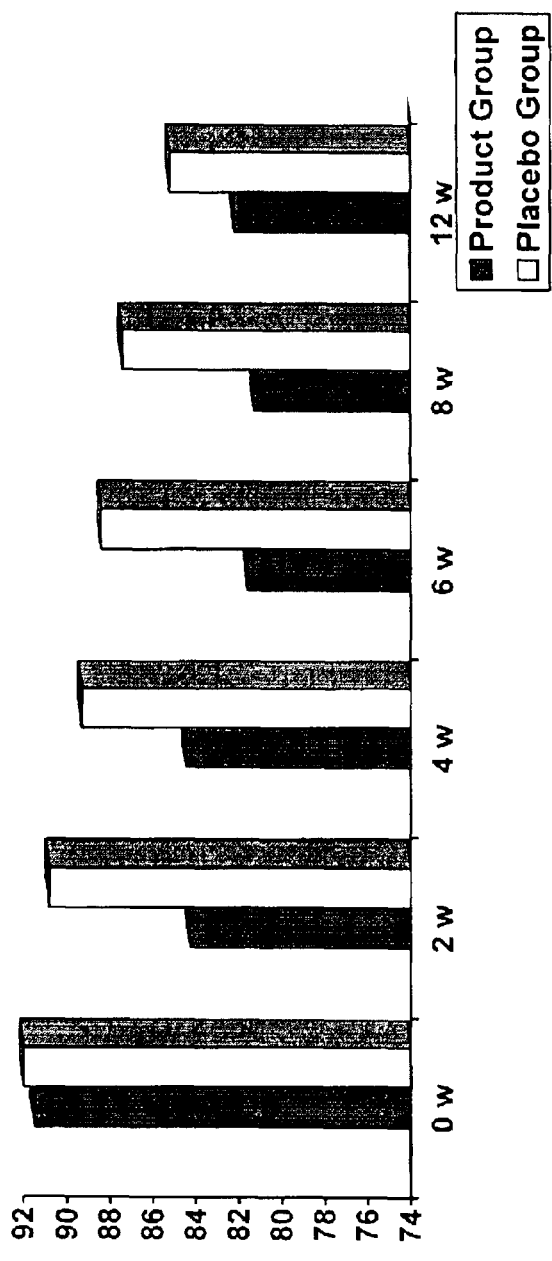
FIG. 2 shows the average diastolic pressure of subjects taking Holistrol ("product group") and placebo.

FIG. 2 shows the average diastolic pressure of subjects taking Holistrol ("product group") and placebo. The data is also summarized in Table 2. The results show that the decrease in blood pressure was sustained even after the Holistrol had been stopped for a month.

TABLE 1

The Group Average of Systolic Blood Pressures

| | Treatment Group (mm Hg) | Placebo (mm Hg) | P Value |
|---|---|---|---|
| 0 Weeks (10, 9) | 142.6 | 142.1 | N.S. |
| 2 Weeks (10, 9)* | 136 | 142.7 | 0.11 |
| 4 Weeks (10, 8) | 133.5 | 143.8 | 0.01 |
| 6 Weeks (9, 8) | 128.4 | 142.9 | 0.002 |
| 8 Weeks (9, 8) | 134.7 | 140.00 | 0.13 |
| 12 Weeks (8, 3) | 132.0 | 142.7 | 0.16 |

*Refers to the number of subjects contributing to this mean: n = treatment, n = placebo

TABLE 2

The Group Average of Diastolic Blood Pressures

| | Treatment Group (mm Hg) | Placebo (mm Hg) | P Value |
|---|---|---|---|
| 0 weeks (10, 9) | 91.5 | 92.0 | N.S. |
| 2 Weeks (10, 9)* | 85.3 | 90.8 | 0.12 |
| 4 Weeks (10, 8) | 84.5 | 89.3 | 0.25 |
| 6 Weeks (9, 8) | 81.6 | 88.4 | 0.051 |
| 8 Weeks (9, 8) | 81.3 | 87.4 | 0.07 |
| 12 Weeks (8, 3) | 82.2 | 85.2 | 0.69 |

*Refers to the number of subjects contributing to this mean: n = treatment, n = placebo Conclusion:

Holistrol is effective for helping people manage mild to moderate hypertension. It is safe, effective, improve mood, enhance energy level, and can improve hypertension within 2–4 weeks. After stopping taking Holistrol, people's blood pressure remain stable and even improving. This suggests that Holistrol does not simply improve blood pressure mechanically. It actually improves patients' health at a more fundamental level.

Without further elaboration, it is believed that one skilled in the art can, using the preceding description, utilize the present invention to its fullest extent. The preceding preferred specific embodiments are, therefore, to be construed as merely illustrative, and not limiting the remainder of the disclosure in any way whatsoever. The entire disclosure of all, cited above, in the appendix, are hereby incorporated by reference in their entirety.

What is claimed:

1. A pharmaceutical composition, comprising:
   effective amounts of Hainan holly leaf, Chinese hawthorn fruit and Garden radish seed, wherein said composition is effective for lowering blood pressure.

2. A composition of claim 1, wherein said amounts of each herb are synergistic.

3. A composition of claim 1, wherein said composition is effective for treating hypertension.

4. A composition of claim 1, wherein said composition is administered orally.

5. A composition of claim 1, further comprising Oriental persimmon.

6. A pharmaceutical composition, comprising:
   40–95% by weight of Hainan holly leaf,
   2–50% by weight of Chinese hawthorn fruit,
   2–50% by weight of Garden radish seed, and
   2–50% by weight of Oriental persimmon, wherein said composition is effective for lowering blood pressure.

7. A pharmaceutical composition of claim 1, comprising:
   85–95% by weight of Hainan holly leaf, 2–5% by weight of Chinese Hawthorn fruit, and 2–5% by weight of Garden radish, wherein said composition is effective for lowering blood pressure.

8. A method of lowering blood pressure in a subject in need thereof, comprising:

administering a pharmaceutical composition of claim 1.

9. A method of lowering blood pressure in a subject in need thereof, comprising:

administering a pharmaceutical composition of claim 5.

10. A method of lowering blood pressure in a subject in need thereof, comprising:

administering a pharmaceutical composition of claim 6.

11. A method of lowering blood pressure in a subject in need thereof, comprising:

administering a pharmaceutical composition of claim 7.

* * * * *